United States Patent [19]

Loor et al.

[11] Patent Number: 4,690,890
[45] Date of Patent: Sep. 1, 1987

[54] PROCESS FOR SIMULTANEOUSLY DETECTING MULTIPLE ANTIGENS USING DUAL SANDWICH IMMUNOMETRIC ASSAY

[75] Inventors: Rueyming Loor, Hercules; Thabiso M'Timkulu, El Sobrante; Susanne K. DeWitt, Berkeley, all of Calif.

[73] Assignee: Cetus Corporation, Emeryville, Calif.

[21] Appl. No.: 596,676

[22] Filed: Apr. 4, 1984

[51] Int. Cl.$^4$ ............... G01N 33/53; G01N 33/545; C12Q 1/42; C12N 15/00
[52] U.S. Cl. ........................ 435/7; 435/21; 435/172.2; 435/240.27; 435/948; 435/810; 436/531; 436/533; 436/548; 436/808; 436/813; 436/815; 436/819; 935/89; 935/110
[58] Field of Search ............... 260/172 R, 172 B; 435/7.21, 172.2, 948, 240, 805, 810; 436/531, 533, 548, 808, 813, 815, 819; 935/89, 110; 530/387

[56] References Cited

U.S. PATENT DOCUMENTS

| | | | |
|---|---|---|---|
| 4,207,307 | 6/1980 | Kaul et al. | 424/1 |
| 4,315,907 | 2/1982 | Fridlender et al. | 424/1 |
| 4,343,896 | 8/1982 | Wolters et al. | 435/7 |
| 4,376,110 | 3/1983 | David et al. | 436/513 |
| 4,446,122 | 5/1984 | Chu et al. | 424/1.1 |
| 4,474,892 | 10/1984 | Murad | 436/513 |

FOREIGN PATENT DOCUMENTS

| | | |
|---|---|---|
| 0044219 | 1/1982 | European Pat. Off. . |
| 0048357 | 3/1982 | European Pat. Off. . |
| 0068291 | 1/1983 | European Pat. Off. . |
| 0045103 | 2/1983 | European Pat. Off. . |
| 0086095 | 8/1983 | European Pat. Off. . |
| 3205849 | 9/1982 | Fed. Rep. of Germany . |
| WO82/02661 | 8/1982 | PCT Int'l Appl. . |
| 2074727 | 11/1981 | United Kingdom . |

OTHER PUBLICATIONS

M. Kuriyama et al., *JNCI*, 68, 99–105 (1982).
C. Blake et al., *Clin. Chem.*, 28, 1469–1473 (1982).
J. Ljunggren et al., *Acta Endocrinologica*, 81, 487–494 (1976).
Hybritech Tandem (TM) Pap Kit brochure (1981) entitled, "Immunoradiometric Assay for the Quantitative Determination of Prostatic Acid Phosphatase".
Abbott Laboratories Trade brochure (10/13/81) on trade name product Abbott PAP-EIA.
Vihko et al., Clinical Chemistry, vol. 27, p. 1744 (1981).
Larsson, *J. Histochem. Cytochem.*, 1981, vol. 29, pp. 408–410.
Dyminski et al., 67th Annual Meeting of the Federation of American Societies for Experimental Biology, Chicago, IL, U.S.A., Apr. 10–15, 1983, Fed. Proc. 42 (3) 1983, Abstract 873.

*Primary Examiner*—Christine M. Nucker
*Assistant Examiner*—Patricia L. DeSantis
*Attorney, Agent, or Firm*—Janet E. Hasak; Albert P. Halluin

[57] ABSTRACT

At least two antigens in a sample may be detected using an immunometric dual sandwich assay containing an effective amount of at least one monoclonal antibody against each antigen, which antibodies are separately conjugated with the same or different signal moieties as labels, and an effective amount of at least one unlabeled monoclonal antibody against each antigen which unlabeled antibodies are immobilized on a single support. Preferably the antibodies are all products of different cell lines and the antigens are prostatic acid phosphatase and prostate antigen.

17 Claims, 2 Drawing Figures

PROCESS FOR SIMULTANEOUSLY DETECTING MULTIPLE ANTIGENS USING DUAL SANDWICH IMMUNOMETRIC ASSAY

BACKGROUND OF THE INVENTION

1. Field of the Invention

This invention relates to immunometric assays for simultaneously detecting and/or measuring the amount of at least two antigens in samples such as serum, urine or other body fluids. This invention is also directed to test kits for conducting such immunomeric assays.

2. Description of Related Disclosures

Immunoassay techniques are increasingly being used for diagnostic purposes to measure the concentration of antigens, particularly those which are physiologically harmful, in various types of body fluids such as serum and urine. Immunoassay methods, which include competitive immunoassays as well as immunometric assays, rely on interaction between the antigen in question and one or more antibodies to form a complex which is detectable by means of a label on the antigen or antibody.

When the antigens have more than one type of binding site they are advantageously detected by immunometric assays. In this method, a soluble antibody labeled with a signal moiety is employed in conjunction with an unlabeled antibody bound to a solid carrier that is insoluble in the fluid being tested. These two types of antibodies form a ternary complex with the antigen which is detected by the label of the soluble antibody. This so-called "sandwich" assay, where the antigen binds two antibodies to its surface at different locations, is described generally by Wide in *Radioimmunoassay Methods*, ed. by Kirkham et al. (Edinburgh: E. & S. Livingstone, 1970) at pages 199–206. U.S. Pat. No. 4,343,896 also describes use of an immunometric assay for detecting an at least bivalent antigen in a liquid sample.

U.S. Pat. No. 4,376,110 describes a technique using a one-to-one sandwich immunometric assay where one monoclonal antibody is presented in a soluble labeled form and the second monoclonal antibody is bound to an insoluble carrier. This technique represents advantages over prior art techniques using polyclonal antibodies in the sandwich assay. For example, the simultaneous and reverse assays using monoclonal antibodies are more sensitive and rapid that the assays using polyclonal antibodies. In addition, the formation of the soluble sandwich complex does not compete with formation of the desired insoluble complex. PCT Patent Publication No. WO 82/02661 teaches a similar assay. European Patent Application No. 0,045,103 published Feb. 3, 1982 describes an immunochemical determination method where at least two types of monoclonal antibodies are used directed against the same antigen to be determined. U.S. Ser. No. 466,798 filed Feb. 16, 1983 to Murad entitled "Two-site Immunoassays Using Monoclonal Antibodies of Different Classes or Subclasses and Test Kits for Performing Same" discloses a further aspect of the sandwich immunometric assay where the two antibodies employed to detect the antigen are of different immunoglobulin classes or subclasses. U.K. Pat. No. 2,074,727, German Patent Publication No. 3205849, and European Patent Publication Nos. 48,357 and 44,219 describe similar such assays.

It is often desirable, however, to detect more than one antigen in a fluid simultaneously due to small sample volume, low reagent cost and short overall assay time. M. Kuriyama et al., *JNCI*, 68, 99–105 (1982) describe the advantage of using a combination test of tissue-specific markers to detect the presence of two proteins of human prostate-specific origin, namely, prostatic acid phosphatase and prostate antigen. Kuriyama et al., however, did not detect the two antigens by a simultaneous method but rather combined the results of the separate measurements of each antigen.

Mitsuma et al., *Biochem. Biophys. Res. Commun.*, 46, 2107–2113 (1972), Ljunggren et al., *Acta Endocrinol.*, 81, 487–494 (1976) and Haynes et al., *Ann. Clin. Biochem.*, 14, 12–15 (1977) used indirect competitive radioimmunoassay to measure more than one component in a single tube by labeling antigens with two different iodine isotopes, including $^{131}I$ which has a half life of only 8 days. Vihko et al., *Clin. Chem.*, 27, 1744–1746 (1981) disclose immobilizing two types of antibodies on different sections of test tubes and joining them to produce a single multicomponent tube. The haptens are labeled with $^{125}I$, which is detected by indirect radioimmunoassay. This method represents a relatively complex procedure involving separation of the solid phase carrier.

U.S. Pat. No. 4,315,907 and *J. Immunol. Methods*, 26, 381 (1979) describe a specific binding assay to determine multiple antigens employing solid-phase binding agents corresponding to each antigen which are differentially separable, as well as labeled binding agents for each antigen. Each solid-phase bound species is separated from all the other species after incubation.

C. Blake et al., *Clinical Chemistry*, 28, 1469–1473 (1982) describe the simultaneous enzyme immunoassay of two thyroid hormones which has advantages over radioisotopes in that it is stable and allows for facile differential measurement. In this assay a mixture of two conjugates labeled with two different enzymes is used to detect both antigens simultaneously in a fluid. The enzymes form products easily distinguishable from each other by absorption spectrophotometry. Blake et al. used two assay compounds, i.e., two antibodies immobilized on two separate solid carriers, to detect both antigens, rather than a single assay compound.

Prostate antigen (PA) and prostatic acid phosphatase (PAP) are two distinct antigenic proteins of human prostate-specific origin. Biochemically, PA is a glycoprotein of molecular weight 33,000 with a pI of 6.9, whereas PAP has a molecular weight of 100,000 and a multiple pI ranging from 4.2 to 5.5. Antisera specifically react toward each antigen and to not cross-react with each other. Although not specific to prostate tumors, PAP and PA in combination are promising markers in detecting prostate cancer because they may reflect different aspects of neoplastic transformation in prostate cancer. Thus, detecting both markers simultaneously represents a diagnostic tool of considerable importance.

SUMMARY OF THE INVENTION

Accordingly, the present invention discloses an improved process for simultaneously detecting more than one antigen, most preferably PA and PAP, over the assay processes described in existing publications. A single immunometric assay material is used herein to detect all of the antigens in the test fluid. Thus, the optimization of amounts of conjugates to be used in the assay mixture for the antigens is simplified. Furthermore, in the assay herein the measurement is direct rather than an indirect competitive immunoassay.

Specifically, in one aspect the present invention represents an improved immunometric assay for simultaneously detecting the presence of at least two antigens in a sample, which assay comprises contacting the sample with at least two labeled monoclonal antibodies, each being directed against a different antigen in the sample and each being separately conjugated with the same or different signal moieties as labels, and with at least two immobilized monoclonal antibodies, each being directed against a different antigen in the sample and each being immobilized on the same support.

In a preferred embodiment the antigenic materials are prostatic acid phosphatase and prostate antigen.

In a second aspect the present invention represents a direct immunometric assay for simultaneously detecting the presence of at least two antigens in a sample which comprises the steps of:

(a) incubating the sample with at least two immobilized monoclonal antibodies, each being directed against a different antigen in the sample and each being immobilized on the same support;

(b) incubating the incubation product of step (a) with at least two labeled monoclonal antibodies, each being directed against a different antigen in the sample;

(c) detecting the amount of labeled antibodies associated with the incubation product of step (b) or the amount of unassociated labeled antibodies; and (d) determining the amount of antigens in the sample by relating the measured amounts of labeled antibodies from step (c) with a control or with samples containing known amounts of the antigens.

In a third aspect the present invention represents an improved immunometric assay method for detecting the presence of at least two antigens in a sample comprising the steps of:

(a) forming a complex of a labeled monoclonal antibody against one antigen in the sample, the antigen, and a monoclonal antibody against the same antigen immobilized on a support to which is also immobilized at least one other monoclonal antibody against a different antigen in the sample which antibody is complexed to that antigen, which antigen is in turn complexed to a monoclonal antibody against that antigen; and (b) measuring either the amount of labeled antibodies bound to the complex or the amount of unbound labeled antibodies to detect the presence of the antigens in the sample.

The complex may be formed by a single-step or double-step incubation of the reagents.

A further aspect of the invention is to provide a test kit for conducting an immunometric assay for determining the presence of at least two antigens in a sample, which comprises an effective amount of at least one monoclonal antibody directed against each antigen in the sample and separately conjugated to a single label or to different labels and an effective amount of at least one unlabeled monoclonal antibody directed against each antigen in the sample where the unlabeled antibodies are immobilized on a single support.

In another embodiment of this test kit the unlabeled monoclonal antibodies are present together with an effective amount of a compound capable of immobilizing the unlabeled antibodies on a solid support.

By using the improved single immunometric assay described herein to determine the presence of multiple antigens in a test sample, one can simultaneously detect two or more antigens using one solid support rather than two or more solid supports with antibodies each specific for one antigen. Furthermore, if different labels are used for the assay, the precise amount of each antigen present in the sample can be determined by separately measuring the different signals produced by the labels.

DETAILED DESCRIPTION OF THE PREFERRED EMBODIMENTS

The following terms as used in the specification are defined below.

The term "epitope" refers to a specific site on the antigen to which only certain antibodies can become attached. Thus, the term refers to a specific antigenic determinant.

The term "soluble" describes antibodies which are 100% soluble or are substantially (i.e., at least about 80%) soluble in the fluid medium containing the antigens, and conversely the term "insoluble" describes carriers (or supports) and antibodies which are substantially (at least about 80%) or completely insoluble in the fluid medium.

The sample on which the immunometric assay of this invention is used refers to any liquid or biological sample which contains or may contain the multiple antigens to be detected. The sample includes fluids such as human or animal body fluids, e.g., blood, serum, urine, amniotic fluid, tissue extracts, cerebrospinal fluid, and the like. The samples may require special treatment such as extraction before being analyzed, depending on the tendency of the antigens contained therein toward lability, aggregation or absorption by the storage container.

The antigens or antigenic materials to be assayed by the procedure of this invention may be defined broadly as substances which are recognized and bound by antibodies. Thus, the term "antigen" includes both immunogenic entities (eliciting an immune response) and hapten entities (not eliciting an immune response). Included among such substances are, e.g., hormones, cells, drugs, enzymes, proteins, peptides, cell surface antigens and other cellular components, differentiation antigens, lymphokines, growth factors, bacteria, viruses, immunoglobulins, allergens, microbial antigen, toxins such as, e.g., those associated with tetanus and venom, other pathogens, and mixtures of two or more different types of these antigens. Examples of specific antigens which may be assayed include Immumoglobulin E, tumor antigen, insulin, human thyroid stimulating hormone, parathyroid hormone, nerve growth factor, human growth hormone, tetanus toxin, albumin, ovalbumin, ferritin, GFA protein, S-100 protein, blood coagulation factor VIII, human chorionic gonadotropin, alpha-fetoprotein, carcinoembroyonic antigen, hepatitis A and B, and proteins of human prostate tissue such as prostatic acid phosphatase and prostate antigen, as described in European Patent Publication No. 0,042,428 and by K. Kuriyama et al., *JNCI,* 68, 99-105 (1982). Preferably the antigens present in the sample will each be multideterminant, i.e., will contain at least two epitopes which differ immunologically and are recognized and bound by complementary antibodies. Most preferably the mixture of antigens comprises prostatic acid phosphatase and prostate antigen.

As an illustration of one type of assay herein, the simultaneous dual sandwich immunometric assay of two antigens consists of one monoclonal antibody against one antigen and another monoclonal antibody against another antigen which are both immobilized on one support, such as polystyrene beads, and of one monoclonal antibody against one antigen and another monoclonal antibody against another antigen separately conjugated with either the same or different detection signals, as labels, whether they be, for example, enzymes, radioactive labels or fluorescent compounds.

The monoclonal antibodies which are employed in the assay of this invention are generally obtained according to the somatic cell hybridization procedure described by Milstein et al., *Nature,* 256, 495-497 (1975) and Koehler et al., *Eur. J. Immunol.,* 6, 511-519 (1976). Basically in this procedure a mouse or other appropriate host animal is injected with an immunogen and then sacrificed. The resulting antibody-producing cells, taken, e.g., from its spleen or lymphoid tissue, are fused with appropriate selectable cancer (myeloma) cells using a suitable fusogen such as polyethylene glycol to form a hybridoma. Preferred myeloma cells are those which fuse efficiently, support stable high level expression of antibody by the selected antibody-producing cells, and are sensitive to a medium such as HAT medium. Among these, preferred myeloma cell lines are murine myeloma lines such as those derived from MOPC-21 and MPC-11 mouse tumors available from the Salk Institute Cell Distribution Center in San Diego, Calif. The hybridomas thus prepared are washed to remove the fusogen and then seeded and grown in the selective media such as HAT to select only those hybridomas resistant to the medium and immortal.

The hybridomas thus selected are screened for production of individual antibodies directed against the specific antigens by, e.g., radioimmunoassay and/or enzyme immunoassay and are generally screened for affinity by similar techniques. Positive clones which produce antibodies that bind to different epitopes of one particular antigen may be selected, in one technique by illustration only, by incubating the antigen first with unlabeled antibody from one of the clones and next with labeled antibody from another clone to determine whether binding of the labeled antibody was blocked by binding of the unlabeled antibody. It is noted that the labeled monoclonal antibodies of this invention may not only be whole immunoglobulin, but may also be monovalent or divalent fragments of the antibodies which bind to the antigen. Such fragments may be prepared by digesting the monoclonal antibody desired with suitable enzymes and isolating the desired fragment from the digest.

After the hybridomas are screened to isolate individual clones which secrete the antibodies of the desired specificity, reactivity, and affinity, the clones may be subcloned by limiting dilution procedures and grown by known procedures. The monoclonal antibodies secreted by the subclones may be separated from the culture medium, ascites fluid or serum by conventional immunoglobulin purification procedures such as, e.g., ammonium sulfate precipitation, gel electrophoresis, dialysis, DEAE cellulose chromatography or affinity chromatography.

The antibodies produced by and isolated from the individual hybridoma cell lines in turn are screened for their affinity for the immunogenic substance which had stimulated the production of the antibodies. In a preferred embodiment the monoclonal antibody selected from the screening will have an affinity of at least about $10^8$ liters per mole, more preferably at least $10^9$ liters per mole.

Whether the unlabeled immobilized monoclonal antibody directed against one antigen can be different from the labeled monoclonal antibody directed against the same antigen will depend mainly on the type of antigen being employed. For example, if the antigen contains two or more identical epitopes which are sufficiently distant from each other to permit the same antibodies to bind simultaneously, such as PAP, then the same antibodies can be used for both the labeled and unlabeled antibodies directed against the same antigen. If, however, the antigen contains epitopes which are all different from each other, such as PA, the antibodies are necessarily different from each other. Preferably the monoclonal antibodies directed against each antigen are different, and most preferably all the monoclonal antibodies employed in the assay are from different cell lines.

The labeled monoclonal antibodies directed against each antigen employed for the assay herein are monoclonal antibodies which are usually soluble in the fluid to be tested and are labeled with signal moieties which may be the same or different for each antibody and which can be conveniently detected for diagnostic purposes. Thus, each antibody may be conjugated separately with the same label moiety, or each may be conjugated separately to different labels for ease of differential measurement. Included among such signal moieties are, for example, enzyme labels, such as alkaline phosphatase, biotinavidin, β-galactosidase or horseradish peroxidase, detectable by addition of a substrate; spectroscopic or photochemical labels, such as a fluorescent label, e.g., fluorescein isothiocyanate or rhodamine, detectable by fluorimetry, or chemiluminescent labels such as luciferin; radioactive isotopic labels, such as, e.g., $^{125}I$, $^{32}P$, $^{14}C$ or $^{3}H$, detectable by radioactive means; spin labels; bacteriophage labels; and the like. In addition, an indirect assay may be employed wherein labeled antisera against the monoclonal antibody to be labeled are added to the medium, as described in U.S. Ser. No. 466,798, supra, so as to produce the labeled antibody in situ.

To obtain qualitative measurements of each type of antigen present in a sample, using a single label moiety in the assay is sufficient. If it is desirable to perform quantitative measurements of the amounts of each type of antigen present in the sample, however, it may be necessary and is preferred to use the assay having different labels which can be detected by different detection signals. For example, two separate enzymes may be employed in the assay which catalyze their respective substrates, the products of which absorb at different wavelengths. The location and height of the absorbance peaks will determine the type and amount of each antigen present in the sample.

One determining factor as to which signal moiety or moieties to employ is the optimum pH at which each operates. For example, horseradish peroxidase operates at an optimum pH of about 6.0, whereas $\beta$-galactosidase and alkaline phosphatase operate optimally at alkaline pH values, with 8.1 optimum for $\beta$-galactosidase and 10.2 optimum for alkaline phosphatase. If more than one enzyme label moiety is being employed, the substrates for the enzymes are added such that the substrate for the enzyme operating optimally at the lower pH is added first.

Any method known in the art for separately conjugating the antibodies to the signal moieties may be employed, including those methods described by U.S. Pat. Nos. 3,940,475 (fluorimetry) and 3,645,090 (enzymes), Hunter et al., *Nature*, 144, 945 (1962), David et al., *Biochemistry*, 13, 1014–1021 (1974), Pain et al., *J. Immunol. Methods*, 40, 219–230 (1981), and Nygren, *J. Histochem. and Cytochem.*, 30, 407–412 (1982). The number of different labeled antibodies in the assay of the present invention depends on the number of antigens in the sample, but is by necessity at least two, because the sample being tested will contain at least two antigens.

The monoclonal antibodies directed against each antigen which are together immobilized on a single support are generally insoluble in the fluid to be tested, are not labeled with any signal moiety, and are used to extract physically the antigens from the sample. The support or carrier on which the antibodies are immobilized is generally essentially water-insoluble and may be any support known to be useful in immunometric assays, including supports in the form of, e.g., surfaces, particles, porous matrices, etc. Examples of commonly used supports include filter paper, Sephadex, polyvinylchloride, plastic beads or test tubes manufactured from polyethylene, polypropylene, polystyrene and the like, agarose, crosslinked dextran, other polysaccharides, etc. The preferred such support herein is polystyrene beads.

The number of different immobilized antibodies in the assay herein will depend, as with the labeled antibodies, on the number of antigens in the sample, but is by necessity at least two, because the sample to be tested will contain at least two antigens.

The method for conjugating the support to the antibodies, which may occur before or during the assay as desired, is achieved by chemically or physically conjugating the antibody to an essentially water-insoluble surface, matrix or body. The method described in U.S. Pat. No. 3,645,852 or in Rotmans et al., *J. Immunol. Methods*, 57, 87–98 (1983) for conjugating a single antibody to a support may generally be employed, with the following specific modifications. The support is first activated as necessary (e.g., the support is chemically modified as by treating polystyrene beads with nitric acid and a reducing agent). Secondly, the support is mixed with the antibodies to be conjugated therewith. This mixing is generally carried out in a buffer at a suitable pH, preferably 2-(N-morpholino)ethenesulfonic acid at pH 6, and in the presence of a crosslinking agent, preferably 3-(3-dimethylaminopropyl)carbodiimide (EDAC). Approximately equivalent amounts of each antibody are added to this support medium to give a concentration of each which is appropriate for the medium to which they are added, and preferably are added to yield a final concentration of each of 0.005% by weight/volume. After incubation the mixture may be washed with buffer and stored in a buffer.

Any of the known assay methods may be employed in the present invention, including the forward, reverse or simultaneous assay. In a forward assay the immobilized antibodies are first incubated with the sample being tested to extract the antigens therefrom by forming a binary immobilized antibodies:antigens complex. The solid complex formed is then washed to remove the sample and incubated with the solutions of labeled antibodies until an immobilized antibodies:antigens:labeled antibodies complex is formed. This complex is washed to remove the unreacted labeled antibodies and then tested for presence of antigens by, for example, detecting the presence of labeled antibodies relative to a control sample containing no antigen.

In the simultaneous assay the unlabeled immobilized antibodies and the labeled antibodies are both added to the test sample simultaneously and incubated in one step. After incubation the resulting immobilized complex is separated from the liquid and treated, e.g., washed at a suitable pH, to remove selectively the residue of the sample and the nonspecifically bound labeled monoclonal antibodies. The complex thus obtained is then tested for presence of antigens as described above.

In a reverse assay the labeled antibodies are incubated with the test sample. Then the unlabeled immobilized antibodies are added and a second incubation is carried out. After this second incubation period the solid phase is washed of the sample and the presence of antigens is detected as described above.

The amounts of antibodies to be employed are effective amounts for forming a detectable complex with the antigens. These amounts in turn will depend, e.g., on the type of label(s), the type of antigens, the type of antibodies and the type of assay procedure. For example, both the simultaneous and reverse assay procedures, but not the forward assay procedure, require excess amounts of immobilized antibodies over the amount of each labeled antibody sufficient to bind most or all of the antigens present in the sample. Otherwise, a high dose hook effect will occur where artificially reduced quantites of antigens will be measured when very large amounts of antigens are in fact present in the sample.

The conditions for incubation such as time, temperature, pH, reagent addition sequences, separation (or wash) procedures and other conditions employed in the immunometric assay of this invention are generally those described for known immunometric assays. For example, for the forward two-step assay procedure the incubation conditions will favor binding between the antigens and the immobilized monoclonal antibodies, as at reduced temperatures of, e.g., 0° to 25° C., and between the immobilized complex thus produced and the labeled monoclonal antibodies, as at temperatures of about 0° to 40° C. In the reverse two-step method the opposite conditions will be desired. The pH for each method is typically between about 6 and 9, preferably about 7. and the time for the antigen binding reaction to reach equilibrium is generally about 10 minutes to 2 days, depending mainly on the types of antibodies and antigens employed as well as the incubation temperature and pH.

The presence or absence of antigens in the sample may be determined by, for example, examining the immobilizing support by various known means, especially by measuring the amount of each labeled antibody bound to the support and comparing this amount to the amount of each labeled antibody detected in a control free of one or both of the antigens or with standard curves. Detecting labeled antibodies in amounts which are considerably higher than background levels of the negative control indicates qualitatively the presence of one or both of the antigens. If the amount of labeled antibodies is compared with that obtained for standard samples with known amounts of antigens and the labels on the antibodies produce different signals, the amount of each antigen can be quantitatively measured. Alternatively, the amount of antigens in the sample being assayed can be determined by measuring the amount of unassociated labeled antibodies, i.e., those which do not form a complex during incubation and therefore remain in a soluble form. The particular detection technique employed, of course, will depend on the type(s) and number of label(s) employed. With certain labels such as enzyme labels the product must be reacted with an appropriate substrate(s) or ligand(s) to render it detectable and is then subjected to, e.g., spectrophotometric analysis.

In one preferred assay procedure herein one solid phase support immobilizing the unlabeled monoclonal antibodies directed against each antigen, the antigenic fluid or patient sample to be tested (preferably in a buffer), and the labeled monoclonal antibody conjugates, directed against each antigen (and in a buffer and in a total amount equal to the amount of antigenic fluid or sample being employed), are mixed together and simultaneously incubated for from about 30 minutes to about 2 hours at a temperature of 25° to 37° C., preferably for 2 hours at room temperature. The resulting mixture is then washed with buffered solution appropriate for the particular ingredients being added. The washed mixture is then subjected to a detection means for the label(s), such as, e.g., radioactivity to detect radioisotopes, addition of enzyme substrate(s) such as, e.g. ortho-phenylenediamine for horseradish peroxidase, phenolphthalein monophosphate for alkaline phosphatase or p-nitrophenyl $\beta$-D galactopyranoside for $\beta$-galactosidase to form a colored product which may be detected by its absorbance or visible color change, or fluorescence for the fluorescent labels. The amount of signal(s) will directly relate to the concentrations of antigens in the sample. If a substrate is employed to detect an enzyme, a solution of the substrate may be added to the washed assay and the mixture then incubated for 15 to 30 minutes at 25°–37° C., preferably for 30 minutes at room temperature. If more than one enzyme label is employed, a solution of a different substrate for the second enzyme is then added and the mixture incubated as described above. Then a solution which terminates the enzyme action such as an acid may be added and the absorbance of the solution measured shortly thereafter to determine the amount of bound antigens.

In another preferred assay procedure herein the solid phase support immobilizing the unlabeled antibodies and the antigenic fluid of patient sample to be tested are mixed together, incubated as described for the simultaneous assay and then aspirated. To the aspirated mixture is then added the labeled antibody conjugates and the resulting mixture is incubated as described for the simultaneous assay. The mixture is then washed with appropriate buffer solution, and the washed mixture is then subjected to appropriate detection means for the label(s) as described above.

The examples which follow further illustrate the embodiments of the invention. In the examples all parts and percentages are by weight per volume and all temperatures in degrees Celsius unless otherwise noted.

EXAMPLE 1

Prostatic acid phosphatase (PAP) and prostate antigen (PA) were selected as the antigens to be detected. Each of these antigens has at least three distinct epitopes. For use in this invention the PA and PAP were obtained from human semen fluid from Pathology Institute, a fertility clinic which is a part of Alta Bates Hospital in Berkeley, Calif.

A. Preparation of Purified PA and PAP Antigens

All of the steps described below are carried out at 4° C. The entire procedure was carried out in three weeks. During the purification of PAP and PA the molecular weight, enzyme activity, and/or immunological reactivity to commercially available antibodies were used to monitor the location of PAP and PA in the various steps and fractions.

About 50 frozen human semen samples containing PAP and PA, obtained as described above in the preface to the example, were thawed in the upright position. To each sample was added 5 ml of 50 mM sodium acetate buffer at pH 5.0 containing sodium acetate and sodium chloride. The samples were removed from their containers and pooled; the empty containers were each rinsed with 20 ml of the sodium acetate buffer; and the rinse wash and samples were combined. The combined samples were centrifuged at 10,000 rpm for 20 minutes, the pellet was discarded, and the supernatant was collected and its volume measured. To the supernatant was added solid ammonium sulfate in an amount of 0.114 g ammonium sulfate per ml of supernatant to yield a final 20% saturation. The mixture was stirred and allowed to stand for 30 minutes. The resulting solution was centrifuged at 14,000 rpm for 20 minutes, the pellet was discarded, and the supernatant was collected and measured for its volume. To the supernatant was added 0.424 g ammonium sulfate per ml of supernatant to yield a final 80% saturation. The mixture was stirred until complete dissolution and then allowed to stand for 30 minutes. Thereafter, the mixture was centrifuged at 14,000 rpm for 20 minutes, the supernatant was discarded, and the pellet was dissolved in about 200 ml of a Tris buffer consisting of 20 mM Tris-HCl at pH 7.5 containing 0.5M NaCl, 1 mM McCl$_2$, 1 mM MgCl$_2$ and 1 mM CaCl$_2$.

The dissolved pellet was then dialyzed against 1 liter of the same Tris buffer using three changes of buffer. The sample was then loaded on a ConA-Sepharose column previously equilibrated with the Tris buffer. The column was washed with the Tris buffer until the absorbance of the elution at 280 nm was less than 0.02 Absorbance units. The column was then eluted with 0.5M $\alpha$-methyl-D-glucoside in the Tris buffer. The bound fractions containing PAP and PA were pooled and the pooled sample was concentrated to about 50 ml using an Amicon concentrator. The sample was then split into 7 ml aliquots and each aliquot was loaded on a Sephacryl S-300 column previously calibrated with molecular weight markers. The columns were eluted with 50 mM of the sodium acetate buffer described above at pH 6.0. The fractions at molecular weight 100,000 containing PAP were pooled, and the fractions at molecular weight 33,000 to 34,000 containing PA were pooled.

Each pooled sample was dialyzed against 1 liter of 20 mM Tris-HCl buffer at pH 7.5 with three changes of buffer and then was loaded on a DEAE-Sepharose column previously equilibrated with 20 mM Tris-HCl buffer at pH 7.5. The columns were then washed with 20 mM Tris-HCl buffer at pH 7.5 until the absorbance of the elution at 280 nm was less than 0.02 Absorbance units.

The column with the PAP sample was eluted with salt gradient (75 mM to 250 mM NaCl in 20 mM Tris-HCl at pH 7.5). The fractions containing PAP were pooled. PAP was shown to consist of only one band by polyacrylamide gel electrophoresis under denaturing conditions. This material is referred to herein as purified PAP.

The column with the PA sample was eluted with salt gradient (0 to 200 mM NaCl in 20 mM Tris-HCl at pH 7.5). The fractions containing PA were pooled. PA was shown to be homogeneous by polyacrylamide gel electrophoresis under denaturing conditions. This material is referred to herein as purified PA.

B. Preparation of Antibodies

Two monoclonal antibodies directed against PAP from different cell lines and two monoclonal antibodies directed against PA from different cell lines were prepared essentially by the somatic cell hybridization method described by G. Koehler et al., *Eur. J. Immunol.*, 6, 511-519 (1976), but using myeloma cells from a different cell line. For the antibodies used in the assay technique of this invention, BALB/c mice purchased from Charles River Lab, Cambridge, Mass. were initially injected intraperitoneally with a mixture of 50 $\mu$g of purified PA or 50 $\mu$g of purified PAP and an equal volume of Freund's adjuvant complete (commercially obtained). After 2 weeks the mice were injected intraperitoneally with a mixture of 20 $\mu$g of purified PAP or 20 $\mu$g of purified PA and an equal volume of Freund's adjuvant incomplete. The mice were then injected with the same antigen mixtures at several weekly intervals thereafter up to about 49-52 days after the initial injection. The last injection consisted of 10 $\mu$g of purified PA or 10 $\mu$g of purified PAP and an equal volume of Freund's adjuvant incomplete. Two or three days after the final immunization, the mice were sacrificed, and their spleens were removed. The spleen cells were suspended in Dulbecco's Modified Eagle's Medium (DMEM) and fused to SP2/0Ag14 myeloma cells (available commercially, deposited in the American Type Culture Collection, 12301 Parklawn Drive, Rockville, Md. 20852 as ATCC No. CRL 1581, and derived by cloning the murine myeloma SP-2 cell line and selecting the one clone which is sensitive to hypoxanthine-aminopterin-thymidine (HAT) medium) in a ratio of spleen to myeloma of 1:1 by cell number, using polyethylene glycol of molecular weight 1000 as a fusogen. The fusion product was plated in a microtiter plate well and then contacted with a solution of $1.0 \times 10^{-4}$M hypoxanthine, $4 \times 10^{-7}$M aminopterin and $1.6 \times 10^{-5}$M thymidine (HAT) in DMEM. The clones in the plate well were then grown in mass culture and centrifuged.

The supernatant was then screened for positive clones using the enzyme-linked immunosorbent assay (ELISA) method. In this method 2.5 $\mu$g of purified PAP or PA per ml of phosphate buffer containing saline (PBS) at pH 7.5 was bound to individual wells of polystyrene microtiter plates by incubating them in 0.1M sodium carbonate at pH 9.6 overnight. Binding of weakly reacted antibodies to the plates was reduced by washing the wells between selected steps with a Tween detergent containing 0.05M PBS at pH 7.5. After the plates were coated with antigen, the hybridoma supernatant, diluted 1:3 by volume with DMEM, was added to the wells and incubated at room temperature for 1-2 hours. The wells were then washed with the detergent described above. Specifically bound PA or PAP antibodies were detected by adding rabbit anti-mouse IgG-horseradish peroxidase to the wells and incubating for 30 minutes. The wells were again washed with the detergent described above and 0.2 ml of 2,2-azino-di-(3-ethylbenzthiazoline sulfonic acid) substrate was added to the wells. The wells were then submitted for spectrophotometric analysis. For this purpose optical density (in Absorbance units) was measured at 414 nm on a Micro Elisa reader. The background was found to be about 0.1 Absorbance units. A highly intense color of the well indicated a high density of highly positive clones of the antibodies. Wells showing an optical density greater than that of the background were saved. Sixty-nine out of 1233 clones against PAP and 33 out of 526 clones against PA were identified as positive in this initial microtiter plate assay screening. Of these positive clones, those having an optical density greater than 1.5 Absorbance units were saved, indicating that they have high reactivity. Twenty-seven out of the 69 positive clones against PAP and 24 out of the 33 positive clones against PA were found to have high reactivity.

The highly reactive clones thus saved were tested for their affinities to PA or PAP by solid phase radioimmunoassay (RIA) techniques by being added to a buffer containing a radioactive tracer (labeled PA or PAP antigen), a solid phase support bound to the second antibody, and an inhibitor (unlabeled antigen) and incubated for 2 hours at 20° C. and centrifuged. The radioactivity of the labeled antigen bound to the solid phase was determined. From this experiment the average affinity of each antibody for the antigen stimulating its original production (PA or PAP) could be calculated. Further details describing the precise competitive radioimmunoassay technique employed are provided in R. Mueller, *J. Immunol. Methods*, 34, 345-352 (1980). Of the 27 clones which were found to bind selectively to PAP in the test described above, seven had an affinity to PAP of at least $1 \times 10^9$ liters per mole. Of the 24 clones which were found to bind selectively to PA in the test described above, nine had an affinity to PA of at least $1 \times 10^9$ liters per mole.

The sixteen clones thus screened were also tested for genetic stability, isotype and sensitivity for PA or PAP detection. Genetic stability is the ability of the clones to produce tumors when injected into mice and kept in tissue culture and to produce monoclonal antibodies for six months after original isolation of the clones. The monoclonal antibodies were detected by RIA as described by R. Mueller, supra, or by enzyme immunoassay (EIA) as described herein for the entire six-month period. All sixteen clones were found to be genetically stable.

The sixteen clones were also tested for their specificity for binding to particular epitopes of their respective antigens by competitive or additive binding and immunoprecipitation studies well known in the art, and for their detection sensitivity by EIA techniques as described herein. Finally, the sixteen clones which bound selectively to PAP or PA were isotyped using a commercial kit with known procedures and all were found to be IgGs of the subclass 1.

Among the nine monoclonal antibodies directed against PA prepared from positive clones and screened for affinity, selectivity, and stability, as well as isotype and sensitivity, were two designated as CETUS RLSD06 (Anti-PA 1) and CETUS RLSD09 (Anti-PA 2), which are directed against two different epitopes of APA. Among the seven monoclonal antibodies directed against PAP prepared from positive clones and screened for affinity, selectivity, and stability, as well as isotype and sensitivity, were two designated as CETUS RLTM01 (Anti-PAP 1) and CETUS RLTM02 (Anti-PAP 2), which are directed against two different epitopes of PAP. Samples of the clones that produced these four antibodies were deposited with the American Type Culture Collection, 12301 Parlawn Drive, Rockville, Md. 20852, U.S.A., and the deposit numbers assigned to them and the dates of deposit, as well as the minimum detection levels (i.e., higher levels can be detected) and affinities of each antibody, are indicated further hereinbelow in Table I.

TABLE I
Monoclonal Antibodies to PAP and PA

| Description of Antibody | Minimum Detection of Antigen (ng/ml) | Affinity (liters/mole) |
| --- | --- | --- |
| CETUS RLTM01 (Anti-PAP 1) (deposited as a hybridoma having ATCC No. HB8526 on March 15, 1984) | 0.5 | $0.3 \times 10^{10}$ |
| CETUS RLSD06 (Anti-PA 1) (deposited as a hybridoma having ATCC No. HB8527 on March 15, 1984) | 0.5 | $1.1 \times 10^{10}$ |
| CETUS RLTM02 (Anti-PAP 2) (deposited as a hybridoma having ATCC No. HB8523 on March 15, 1984) | 0.5 | $0.42 \times 10^{10}$ |
| CETUS RLSD09 (Anti-PA 2) (deposited as a hybridoma having ATCC No. HB8525 on March 15, 1984) | 0.5 | $0.41 \times 10^{10}$ |

All of the hybridoma cell lines above described were deposited with the American Type Culture Collection (ATCC) of Rockville, MD 20852. Each hybridoma cell line deposited with ATCC has the individual ATCC designations indicated in Table I pursuant to a contract between the ATCC and the assignee of this patent application, Cetus Corporation. The contract with ATCC provides for permanent availability of the progeny of these hybidoma cell lines to the public on the issuance of the U.S. patent describing and identifying the deposits or the publications or upon the laying open to the public of any U.S. or foreign patent application, whichever comes first, and for availability of the progeny of these hybridoma cell lines to one determined by the U.S. Commissioner of Patents and Trademarks to be entitled thereto according to 35 U.S.C. 122 and the Commissioner's rules pursuant thereto (including 37 CFR 1.14 with particular reference to 886 OG 638). The assignee of the present application has agreed that if any of these hybridoma cell lines on deposit should die or be lost or destroyed when cultivated under suitable conditions, it will be promptly replaced on notification with a viable culture of the same hybridoma cell line.

Following identification and screening of positive clones, the cells were subcloned several times to ensure their monoclonal nature and then grown in mass culture and injected intraperitoneally into Balb/c mice to produce antibody-rich ascitic fluid. This fluid, which was recovered from the mouse by syringe, contained the desired monoclonal antibody as well as globulin and other proteins.

The specific monoclonal antibodies desired were purified from the ascitic fluid as follows, each step being conducted at 4° C. A total of 10 ml of the mouse actitic fluid was centrifuged at 14,000 rpm for 10 minutes. The resulting pellet was discarded and the volume of supernatant determined. Solid ammonium sulfate was added in an amount of 0.243 g to 1 ml of supernatant to yield a final 40% saturation. The resulting mixture was stirred and then allowed to stand for 30 minutes. Then it was centrifuged at 14,000 rpm for 20 minutes. The supernatant was discarded and the pellet was dissolved in 10 ml of 20 mM sodium phosphate at pH 7.5. This solution was dialyzed against 1 liter of 20 mM sodium phosphate at pH 7.5, with three changes of buffer, and the resulting sample was collected. Thereafter the sample was centrifuged at 14,000 rpm for 20 minutes and the pellet discarded. The protein concentration and volume of the supernatant were measured and it was loaded on a DEAE Affi-Gel Blue column of appropriate size. Then the column was eluted with 20 mM sodium phosphate at pH 7.5 until the absorbance of the solution at 280 nm as measured by spectrophotometer was less than 0.02 Absorbance units. The fractions of the first absorbance peak with a maximum absorbance of almost 1.0 Absorbance units, excluding the fractions representing a very small peak at the beginning, were pooled and concentrated in a concentrator to about 10 ml. The resulting sample was measured for protein content and for immunological reactivity by radioimmunoassay methods known in the art. Each monoclonal antibody purified in this manner was found to be pure and be immunologically active.

C. Conjugation of Antibodies to Immobilizing Support

One antibody to PAP (CETUS RLTM01 (Anti-PAP 1)) and one antibody to PA (CETUS RLSD06 (Anti-PA 1)) were conjugated to polystyrene beads by the following two-step procedure:

I. Chemical modification of polystyrene beads

To 4000 polystyrene beads of 6.4 nm diameter obtained commercially was added 1 liter of a solution of 10% fuming nitric acid in glacial acetic acid. This solution was then incubated for 2 hours at 50° C. and then washed about ten times with distilled water. A total of 1 liter of a solution of 1% sodium dithionite in 0.1N sodium hydroxide (as a reducing agent) was added to the solution and the resulting mixture was incubated for 2 hours at 50° C. Then the sample was washed with distilled water about ten times.

II. Covalent bonding of monoclonal antibodies to modified polystyrene beads

To the polystyrene beads modified as described above was added, sequentially with 10 mM 2-(N-morpholino)ethenesulfonic acid buffer at pH 6; 3-(3-dimethylaminopropyl)carbodiimide (EDAC) to a final concentration of 0.1%. Then both the monoclonal antibodies (to a final concentration of each of 0.005%) were added. The total amount of solution added was 600 ml. This mixture was incubated for one hour at room temperature and then washed five times with 50 mM Tris-HCl at pH 7.5. A mixture of 1% bovine serum albumin (BSA) in a Tris buffer consisting of 50 mM Tris-HCl at pH 7.5, 0.1M NaCl and 0.05% of a preservative was then added to the washed mixture and the resulting mixture was stored at 4° C. until use.

D. Conjugation of Antibodies to Enzyme Label

All of the steps described in this procedure were carried out at 4° C. unless otherwise indicated. All of the buffers and reagents employed in the procedure were flushed with nitrogen and then sealed with paraffin. Horseradish peroxidase (HRP) enzyme was used as the assay signal.

I. Preparation of horseradish peroxidase enzyme fraction

The horseradish peroxidase employed, obtained commercially, had a molecular weight of 40,000 and a concentration of 25.5 mg per ml in a conjugation buffer of 0.1M sodium phosphate and 0.1M sodium chloride at pH 7.5. The HRP solution was dialyzed against the same conjugation buffer and recovered in an amount of about 1.7 ml. To the HRP solution was added 315 μl of a 40 mM solution of N-succinimidyl-3-(2-pyridyl-dithio)propionate (SPDP) in 100% ethanol, to yield a ratio of SPDP: peroxidase of 12,600 μM: 630.5 μM (20:1 molar ratio). The mixture was then stirred and incubated for 30 minutes at room temperature and then loaded on a Sephadex G-25 column with 50 ml bed volume previously equilibrated with a sodium acetate buffer consisting of 0.1M sodium acetate at pH 4.5 and 0.1M sodium chloride. The void volume peak was collected in about 8 to 13 fractions and then concentrated to about 1.5 ml, and the concentrator was rinsed with 0.5 ml sodium acetate buffer. Then, in a reduction step, a freshly prepared stock buffer consisting of 0.5M dithiothreitol in the sodium acetate buffer was added to a final concentration of 50 mM dithiothreitol. The mixture was then stirred and incubated for 20 minutes at room temperature. Immediately after incubation the mixture was loaded on a Sephadex G-25 column with a 50 ml bed volume previously equilibrated with sodium phosphate. The void volume peak was pooled from about 8 to 12 fractions and concentrated to 2.5 ml.

II. Preparation of monoclonal antibody fraction

The desired monoclonal antibodies (CETUS RLTM02 (Anti-PAP 2) and CETUS RLSD09 (Anti-PA 2)), screened and purified as described above and in a concentration of 10 mg per ml of the conjugation buffer described above, were dialyzed against the same conjugation buffer and recovered in an amount of about 1.25 ml. To each purified antibody (immunoglobulin G) was added 7.9 μl of a 40 mM solution of SPDP in 100% ethanol, to yield a molar ratio of antibody to SPDP of 1:5. Each mixture was then stirred and incubated for 30 minutes at room temperature and then loaded on a Sephadex G-25 column with 50 ml bed volume previously equilibrated with sodium phosphate buffer. The void volume peak fractions for each antibody were pooled and concentrated to 2.5 ml.

III. Conjugation of enzyme with antibody

This step was carried out twice using the two different antibodies. The HRP enzyme fraction and the antibody fraction obtained from above Steps I and II respectively were combined and stirred, and the mixture was incubated for 22 hours at room temperature. The mixture was then loaded on a Bio-Gel P-300 column with 500 ml bed volume previously equilibrated with 0.05M PBS solution at pH 7.5, and was eluted with PBS for about 3-4 days. The fractions containing the enzyme:antibody conjugate (at the 238,000 molecular weight position) were pooled and tested for sensitivity as described below.

E. Preparation of PA, PAP and PA/PAP Antigen Standards

The procedure described in Sec. A was employed up to and including the step where the mixture of 0.424 g ammonium sulfate per ml of supernatant was centrifuged at 14,000 rpm for 20 minutes and the supernatant was discarded. The pellet thus recovered was dissolved in about 200 ml of PBS using 4-5 strokes slowly in a homogenizer.

The dissolved pellet was then dialyzed against 4 liters of PBS using three changes of PBS. The sample was then centrifuged at 14,000 rpm for 20 minutes and the pellet discarded. The supernatant (300 mg/20 ml) containing PAP and PA was further passed through a Sephadex S-300 column and eluted with PBS at pH 7.5. The PAP antigen standard was pooled from the fractions at molecular weight 100,000 and the PA antigen standard was pooled from the fractions at molecular weight 34,000. A small aliquot from the pooled PAP and PA antigen standard samples was analyzed for antigen concentration by RIA or EIA using purified PA and PAP as a standard or a commercial kit standard.

A 50:50 mixture of PA and PAP by weight was prepared by mixing the two separate PAP and PA antigen standards together.

F. Simultaneous Enzyme Immunometric Assay

In the description below, the Ab designations are shorthand representations for each conjugated antibody as follows:

| Conjugate | Description |
|---|---|
| Ab1 | CETUS RLTM01 (Anti-PAP 1) and CETUS RLSD06 (Anti-PA 1) bound to polystyrene beads |
| Ab2 | CETUS RLTM02 (Anti-PAP 2) separately bound to HRP |
| Ab3 | CETUS RLSD09 (Anti-PA 2) separately bound to HRP |

I. A sandwich immunometric assay, designated Assay PAP+PA, of the type $$Ab1 \genfrac{}{}{0pt}{}{:PAP:Ab2}{:PA:Ab3}$$

was evaluated by the following procedure:

The conjugate of immobilized monoclonal antibodies (Ab1) was removed from the suspension of BSA and Tris buffer. The 50:50 mixture of PAP and PA as antigen standard described in Sec. E was added to 5% BSA in the Tris buffer of 50 mM Tris-HCl of pH 7.5, 0.1M NaCl and 0.05% preservative to yield a total mixture of 200 μl of PA and PAP. The monoclonal antibodies bound to the HRP enzyme (Ab2 and Ab3) were each added to 5% BSA in the Tris buffer to yield 200 μl solutions of each conjugate. Ab1 was combined with these solutions of Ab2 and Ab3 together with the 200 μl of PAP/PA antigen standard, and the resulting mixture was incubated for two hours at room temperature. Then the mixture was washed three times with 4 ml each time of a solution of 0.01M Tris-HCl of pH 7.5, 0.15M sodium chloride, 0.1% BSA, 0.05% nonionic detergent, and 0.05% preservative.

To the washed mixture was added 0.5 ml of a solution of ortho-phenylenediamine (acting as substrate to the HRP) made by dissolving 0.25 g of the substrate powder in 100 ml of a buffer at pH 6.0, consisting of 0.05M sodium citrate, 0.1M sodium phosphate, 0.03% urea hydrogen peroxide and 0.05% thimerosal. The resulting mixture was stirred and incubated for 30 minutes at room temperature and then 1 ml of 1N HCl solution was added to stop the enzyme action. Within 60 minutes of adding the HCl, the absorbance of the solution at 492 nm was measured. The absorbance measures the amount of antigen bound. The quantity of PA and PAP in the sample may be determined from a standard curve constructed in an identical manner with the use of various concentrations of purified PAP and PA. The results were repeated using varying total amounts of PAP and PA (equal amounts of each) from 0 to 200 ng/ml of test solution.

II. A sandwich immunometric assay, designated Assay PA, of the type Ab1:PA:Ab3 was evaluated as a control by the procedure described above in Sec. FI except that 200 μl of PA, but not PAP, was used as antigen standard and 200 μl of Ab3 solution, but not Ab2 solution, was employed. The absorbance analysis was repeated using amounts of PA varying from 0 to 100 ng per ml of test solution.

III. A sandwich immunometric assay, designated Assay PAP, of the type Ab1:PAP:Ab2 was evaluated as a control by the procedure described above in Sec. FI except that 200 μl of PAP, but not PA, was used as antigen standard, and 200 μl of Ab2 solution, but not Ab3 solution, was employed. The absorbance analysis was repeated using amounts of PAP varying from 0 to 100 ng per ml of test solution.

Figure 1:
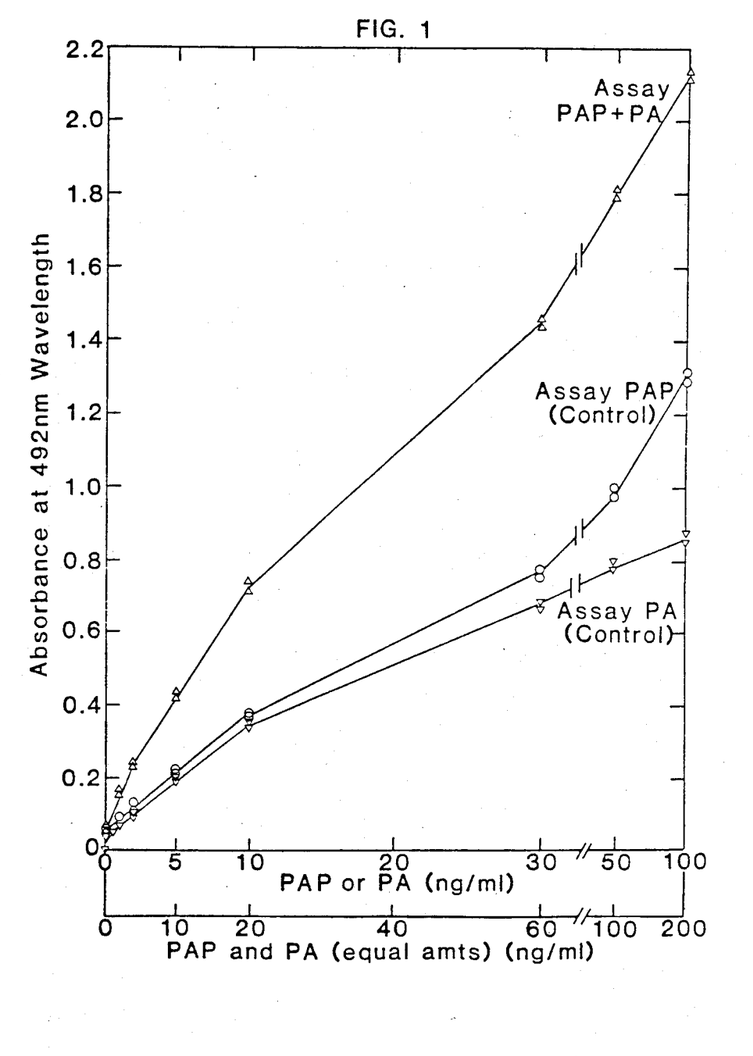
FIG. 1 represents a graphical plot of the spectrophotometric absorbance at 492 nm wavelength of a sample fluid containing prostate antigen (PA), prostatic acid phosphatase (PAP), and a combination of PA and PAP using three sandwich immunometric assays (described in Example 1) against these antigens, respectively, as a function of the amount of antigen or antigen mixture in the sample. The curves designated as Assays PAP and PA represent control assays against PAP and PA, respectively. The immunometric assay against both PAP and PA employed, which is illustrative of this invention and is designated as curve Assay PAP+PA, contains one single type of label.

The plots of absorbance versus concentration of PA, PAP, and PAP+PA for Assay PA, PAP, and PAP+PA, respectively, are provided in FIG. 1. FIG. 1 shows that Assay PAP+PA, the assay representative of this invention which contains two labeled antibodies, exhibits far superior sensitivity toward the multiple antigens than does either control assay, which contains only one labeled antibody, toward its single antigen. Moreover, the assay herein is sufficiently sensitive to detect the presence of antigens in total amounts of less than 1 ng per ml.

G. Two-Step Enzyme Immunometric Assay

In the description below, the Ab designations employed are the same as those used in Sec. F.

A sandwich immunometric assay which is the same as that described in Sec. F, namely was prepared by the following multi-step procedure:

The conjugate Ab1 was removed from the suspension of BSA and Tris buffer. The 50:50 mixture of PAP and PA as antigen standard described in Sec. E was added to 5% BSA in the Tris buffer of 50 mM Tris-HCl of pH 7.5, 0.1M NaCl and 0.05% preservative to yield a total mixture of 200 μl of PA and PAP. Conjugate Ab1 was combined with the antigen mixture, and the mixture was stirred and incubated for one hour at room temperature. A total of 1 ml of water was then added and the mixture was aspirated to remove the solution.

The conjugates Ab2 and Ab3 containing the HRP enzyme label were each added to 5% BSA in the Tris buffer described above to yield 200 μl solutions of each conjugate. Each conjugate was added to the aspirated mixture of Ab1 and antigen standards. The resulting mixture was stirred and incubated for one hour at room temperature. Then the mixture was washed three times with 4 ml each time of distilled water or of the washing Tris buffer employed in Sec. F.

To the washed mixture was added 0.3 ml of a solution of ortho-phenylenediamine (acting as substrate to the HRP) made by dissolving 30 mg of the substrate tablet in 12 ml of a buffer at pH 6.0, consisting of 0.05M sodium citrate, 0.1M sodium phosphate, 0.03% urea hydrogen peroxide and 0.05% thimerosal. The resulting mixture was stirred and incubated for 30 minutes at room temperature and then 1 ml of 1N HCl solution was added to stop the enzyme action. Within 60 minutes of adding the HCl, the absorbance of the solution at 492 nm was measured to determine the amounts of PA and PAP bound. The results of the assay were found to be essentially the same as the results obtained when the simultaneous enzyme immunometric assay of Sec. F was employed.

EXAMPLE 2

This example illustrates the use of a test kit having two different labels in conducting the immunometric assay technique of this invention.

All of the steps described above in Example 1 were employed to prepare the test kit against PA and PAP except that one of the labeled antibody conjugates (containing CETUS RLTM02 (Anti-PAP 2)) contained β-galactosidase as a label and the other labeled antibody conjugate (containing CETUS RLSD09 (Anti-PA 2)) contained alkaline phosphatase as a label, the conjugations being carried out by the following procedures. All steps were carried out at 4° C. unless otherwise indicated and all of the buffers and reagents employed were flushed with nitrogen and then sealed with paraffin.

A. Conjugation of Antibody to Alkaline Phosphatase Enzyme

I. Preparation of alkaline phosphatase enzyme fraction

The alkaline phosphatase employed, obtained commercially, had a molecular weight of 140,000 and a concentration of 19 mg/ml in a conjugation buffer of 0.1M Tris-HCl and 0.1M sodium chloride at pH 7.4. The alkaline phosphatase solution was dialyzed against the same conjugation buffer and recovered in an amount of about 1.7 ml. To the alkaline phosphatase solution was added 85 μl of a 40 mM solution of SPDP in 100% ethanol, to yield a molar ratio of SPDP:alkaline phosphatase of 25:1. The mixture was then stirred and incubated for 30 minutes at room temperature and then loaded on a Sephadex G-25 column with 50 ml bed volume previously equilibrated with a sodium acetate buffer consisting of 0.1M sodium acetate at pH 4.5 and 0.1M sodium chloride. The void volume peak was collected in about 8 to 13 fractions and then concentrated to about 1.5 ml, and the concentrator was rinshed with 0.5 ml sodium acetate buffer. Then, in a reduction step, a freshly prepared stock buffer consisting of 0.5M dithiothreitol (DTT) in the sodium acetate buffer was added to a final concentration of 50 mM DTT. The mixture was then stirred and incubated for 20 minutes at room temperature. Immediately after incubation the mixture was loaded on a Sephadex G-25 column with a 50 ml bed volume previously equilibrated with Tris-HCl. The void volume peak was pooled from about 8 to 12 fractions and concentrated to 2.5 ml.

II. Preparation of monoclonal antibody fraction

The desired monoclonal antibody, CETUS RLSD09 (Anti-PA 2), screened and purified as described in Example 1 and in a concentration of 4.3 mg/ml of the conjugation buffer described above, was dialyzed against the same conjugation buffer and recovered in an amount of about 1.25 ml. To the purified antibody (immunoglobulin G) was added 6.8 μl of a 40 mM solution of SPDP in 100% ethanol, to yield a molar ratio of antibody to SPDP of 1:10. The mixture was then stirred and incubated for 30 minutes at room temperature and then loaded on a Sephadex G-25 column with 50 ml bed volume previously equilibrated with Tris-HCl. The void volume peak fractions were pooled and concentrated to 2.5 ml.

III. Conjugation of enzyme with antibody

The alkaline phosphatase enzyme fraction and the antibody fraction obtained from above Steps AI and AII, respectively, were combined and stirred, and the mixture was incubated for 22 hours at room temperature. The mixture was then loaded on a Bio-Gel P-300 column with 500 ml bed volume previously equilibrated with a buffer consisting of 0.1M Tris-HCl, 0.1M NaCl, pH 7.4, 10 mM magnesium chloride and 1 mM zinc chloride. The column was eluted with the same buffer for about 3-4 days. The fractions containing the enzyme:antibody conjugate (at the 430,000 molecular weight position) were pooled and tested for sensitivity as described in Example 1.

B. Conjugation of Antibody to β-Galactosidase

I. Preparation of monoclonal antibody fraction

The desired monoclonal antibody, CETUS RLTM02 (Anti-PAP 2), screened and purified as described in Example 1 and in a concentration of 10 mg/ml of a conjugation buffer of 0.1M sodium phosphate at pH 7.5 and 0.1M sodium chloride, was dialyzed against the same conjugation buffer and recovered as a solution of purified immunoglobulin G of molecular weight 158,000. To this solution was added 7.9 μl of a 40 mM solution of SPDP in 100% ethanol, to yield a molar ratio of antibody to SPDP of 1:5. The mixture was then stirred and incubated for 30 minutes at room temperature and then loaded on a Sephadex G-25 column with 50 ml bed volume previously equilibrated with the conjugation buffer. The column was eluted with the conjugation buffer and the void volume peak fractions were pooled and concentrated to 2.5 ml.

II. Conjugation of enzyme with antibody

A total of 34 mg per ml of the conjugation buffer of β-galactosidase of molecular weight 540,000 commercially obtained from Boehringer Mannheim in Indianapolis, Ind. and 10 mg per ml of the conjugation buffer of the antibody fraction obtained from above Step I were combined and stirred to yield a 1:1 molar ratio of enzyme to antibody, and the mixture was incubated for 22 hours at room temperature. The mixture was then loaded on a Bio-Gel P-300 column with 500 ml bed volume previously equilibrated with the conjugation buffer described in Sec. BI. The column was eluted with the same buffer for about 3-4 days. The fractions containing the enzyme:antibody conjugate were pooled and tested for sensitivity as described in Example 1.

C. Two-Step Enzyme Immunometric Assay

In the description below, the Ab designations are shorthand representations for each conjugated antibody as follows:

| Conjugate | Description |
| --- | --- |
| Ab1 | CETUS RLTM01 (Anti-PAP 1) and CETUS RLSD06 (Anti-PA 1) bound to polystyrene beads |
| Ab4 | CETUS RLTM02 (ANTI-PAP 2) separately bound to β-galactosidase |
| Ab5 | CETUS RLSD09 (Anti-PA 2) separately bound to alkaline phosphatase |

A sandwich immunometric assay, designated Assay PAP'+PA', of the type $$Ab1 \genfrac{}{}{0pt}{}{:PAP:Ab4}{:PA:Ab5}$$

was evaluated by the following procedure:

The conjugate of immobilized monoclonal antibodies (Ab1) from Example 1 was removed from the suspension of BSA and Tris buffer. The PAP and PA antigen standards described in Sec. E of Example 1 were added to 5% BSA in the Tris buffer of 50 mM Tris-HCl of pH 7.5, 0.1M NaCl and 0.05% preservative to yield a total of 200 μl PAP standard and 200 μl PA standard. The conjugates of monoclonal antibodies labeled with their respective enzymes (Ab4 and Ab5) were each added to 5% BSA in the Tris buffer to yield 200 μl solutions of each conjugate. Ab1 was combined with these solutions of antigens and the resulting mixture was stirred and incubated for two hours at room temperature. Then the mixture was aspirated to remove the solution. The conjugates of monoclonal antibodies labeled with their respective enzymes (Ab4 and Ab5) were each added to 5% BSA in the Tris buffer to yield 200 μl solutions of each conjugate. The solution of Ab4 conjugate and the solution of Ab5 conjugate were added to the aspirated mixture of Ab1 and antigens. The resulting mixture was stirred and incubated for one hour at room temperature. Then the mixture was washed three times with 4 ml each time of the Tris-HCl washing buffer described in Sec. FI of Example 1.

To the washed mixture was added 0.5 ml of a 2.5 mM solution of p-nitrophenyl β-D-galactopyranoside (acting as substrate to the β-galactosidase) in 10 mM Tris-HCl at pH 8.1 containing 5% ethanol, 10 mM MgCl$_2$ and 0.1 mM ZnCl$_2$. The resulting mixture was stirred and incubated for 30 minutes at room temperature. Then 0.5 ml of an 8 mM solution of phenolphthalein monophosphate (acting as substrate to the alkaline phosphatase) in 0.1M diethanolamine at pH 10.2 was added to the mixture. The resulting mixture was stirred and incubated for 30 minutes at room temperature. Then 1 ml of a solution of 0.5M sodium phosphate at pH 10.2 containing 0.1M EDTA was added to stop the enzyme action. Within 60 minutes of adding the stopping solution, the absorbance of the solution at 405 nm was measured to detect β-galactosidase and therefore the presence and concentration of PAP in the sample.

The absorbance of the solution at 550 nm was then measured to detect alkaline phosphatase and thus the presence and concentration of PA in the sample.

Figure 2:
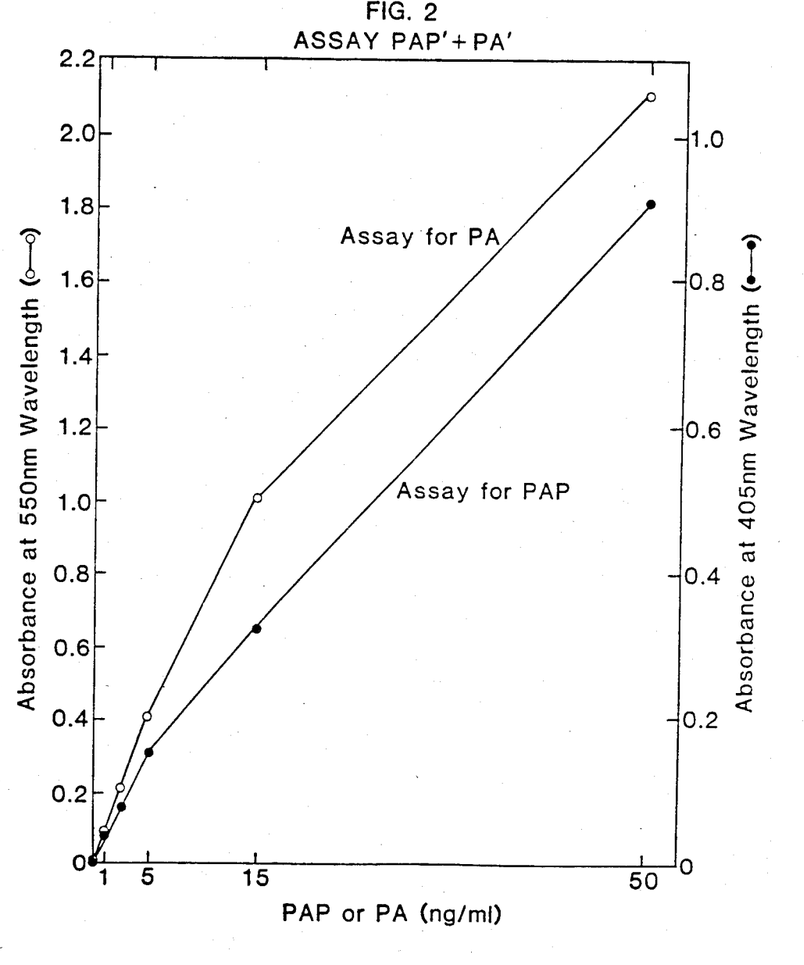
FIG. 2 represents a graphical plot of the spectrophotometric absorbances at 405 nm and 550 nm wavelengths of a sample fluid containing PA and PAP using the sandwich immunometric assay described in Example 2 against these antigens, as a function of the amount of each antigen in the sample. The immunometric assay against both PA and PAP employed, which is illustrative of this invention and is designated as curve Assay PAP'+PA', contains two different types of labels.

FIG. 2 illustrates plots of absorbance at 405 nm (assay for PAP concentration) and 550 nm (assay for PA concentration) of the assay of this example, namely Assay PAP'+PA'. The results indicate that the presence and concentration of PAP and PA in a sample can be simultaneously determined using the assay herein having two different enzyme labels conjugated to the antibodies. The reading at 405 nm measures activity of $\beta$-galactosidase and thus indexes the PAP concentration, and the reading at 550 nm measures activity of alkaline phosphatase and thus indexes the PA concentration in the sample.

It is noted that the above procedure will be successfully carried out if the enzyme labels and antibodies are exchanged. In addition, successful results were obtained when a simultaneous enzyme immunometric assay as described in Sec. FI of Example 1 was employed using the conjugates of this example.

The present invention is seen to provide an improved immunometric assay technique for detecting multiple antigens using as the test kit a single conjugate where at least two monoclonal antibodies directed against at least two antigens are immobilized on a solid support.

What is claimed is:

1. An immunometric assay for detecting the presence of prostatic acid phosphatase and prostate antigen in a sample which comprises contacting the sample with (a) a labeled monoclonal antibody from hybridoma cell line ATCC No. HB 8523, which is directed against prostatic acid phosphatase, (b) a labeled monoclonal antibody from hybridoma cell line ATCC No. HB 8525, which is directed against prostate antigen, (c) an immobilized monoclonal antibody from hybridoma cell line ATCC No. HB 8526 or HB 8523, directed against prostatic acid phosphatase, and (d) an immobilized monoclonal antibody from hybridoma cell line ATCC No. HB 8527, directed against prostate antigen, wherein each immobilized antibody is immobilized on a common support.

2. The assay of claim 1 wherein the label or labels are selected from the group consisting of enzymes, radioactive isotopes and fluorescent compounds.

3. The assay of claim 1 wherein the labels on each monoclonal antibody are the same.

4. The assay of claim 1 wherein the labels on each monoclonal antibody are different.

5. The assay of claim 1 wherein the sample is a body fluid.

6. The assay of claim 1 wherein the immobilized antibodies are immobilized on polystyrene beads.

7. The process of claim 1 wherein the immobilized antibody against prostatic acid phosphatase is from HB 8526.

8. A direct immunometric assay for detecting the presence of prostatic acid phosphatase and prostate antigen in a sample which comprises:
(a) incubating the sample with an immobilized monoclonal antibody from hybridoma cell line ATCC No. HB 8523, which is directed against prostatic acid phosphatase, and with an immobilized monoclonal antibody from hybridoma cell line ATCC No. HB 8525, which is directed against prostate antigen, wherein both antibodies are immobilized on a common support and wherein if both prostatic acid phosphatase and prostate antigen are present, each of the immobilized antibodies will complex with its corresponding antigen;
(b) incubating the incubation product of step (a) with (i) a labeled monoclonal antibody from hybridoma cell line ATCC No. HB 8526 or HB 8523, directed against prostatic acid phosphatase, and (ii) a labeled monoclonal antibody from hybridoma cell line ATCC No. HB 8527, directed against prostate antigen, wherein if both prostatic acid phosphatase and prostate antigen are present, each of the labeled antibodies will complex with its corresponding antigen;
(c) detecting the amount of labeled antibodies associated with the incubation product of step (b) or the amount of unassociated labeled antibodies; and
(d) determining the amount of antigens in the sample from the amount of labeled antibodies detected from step (c).

9. The assay of claim 8 wherein at least one label is selected from the group consisting of enzymes, radioactive isotopes and fluorescent compounds.

10. The assay of claim 8 wherein the immobilized antibody against prostatic acid phosphatase is from HB 8626.

11. An immunometric assay for detecting the presence of prostatic acid phosphatase and prostate antigen in a sample which comprises:
(a) forming a complex of (1) a labeled monoclonal antibody from hybridoma cell line ATCC No. HB 8523, which is directed against prostatic acid phosphatase and is complexed to (2) prostatic acid phosphatase, which is in turn complexed to (3) an unlabeled monoclonal antibody from hybridoma cell line ATCC No. HB 8523 or HB 8526 whichis directed against prostatic acid phosphatase and immobilized on a support to which is also immobilized (4) an unlabeled monoclonal antibody from hybridoma cell ATCC No. HB 8527, which is directed against prostate antigen and is complexed to (5) prostate antigen, which is in turn complexed to (6) a labeled monoclonal antibody from hybridoma cell line ATCC No. HB 8525, which is directed against prostate antigen; and
(b) measuring either the amount of labeled antibodies bound to the complex or the amount of unbound labeled antibodies to detect the presence of prostatic acid phosphatase and prostate antigen in the sample.

12. The assay of claim 11 wherein the immobilized antibodies, antigens and labeled antibodies are incubated simultaneously to form the complex.

13. The assay of claim 11 wherein the immobilized antibody against prostatic acid phosphatase is from HB 8526.

14. A test kit for conducting an immunometric assay for detecting the presence of prostatic acid phosphatase and prostate antigen in a sample, which comprises, in packaged combination, a multicontainer unit having:
(a) a first container containing a monoclonal antibody from hybridoma cell line ATCC No. HB 8523 directed against prostatic acid phosphatase and separately conjugated to a label;
(b) a second container containing a monoclonal antibody from hybridoma cell line ATCC No. 8525 directed against prostate antigen and separately conjugated to a label; and
(c) a third container containing a single support on which is immobilized an unlabeled monoclonal antibody from hybridoma cell line ATCC No. HB 8523 or HB 8526 directed against prostatic acid phosphatase, and an unlabeled monoclonal antibody from hybridoma cell line ATCC No. HB 8527, directed against prostate antigen.

15. The test kit of claim 14 wherein at least one label is selected from the group consisting of enzymes, radioactive isotopes and fluorescent compounds.

16. The test kit of claim 14 wherein the labels on each labeled monoclonal antibody are different.

17. The test kit of claim 14 wherein the immobilized antibody against prostatic acid phosphatase is from HB 8526.

* * * * *